US008494247B2

(12) United States Patent
Watanabe (10) Patent No.: US 8,494,247 B2
(45) Date of Patent: Jul. 23, 2013

(54) RADIOGRAPHIC IMAGING APPARATUS AND PROCESSING METHOD THEREFOR

(75) Inventor: Yukako Watanabe, Yokohama (JP)

(73) Assignee: Canon Kabushiki Kaisha, Tokyo (JP)

(*) Notice: Subject to any disclaimer, the term of this patent is extended or adjusted under 35 U.S.C. 154(b) by 377 days.

(21) Appl. No.: 12/851,260

(22) Filed: Aug. 5, 2010

(65) Prior Publication Data

US 2011/0052034 A1  Mar. 3, 2011

(30) Foreign Application Priority Data

Aug. 31, 2009  (JP) .................................. 2009-201094

(51) Int. Cl.
*G06K 9/00* (2006.01)
(52) U.S. Cl.
USPC ................................ 382/132; 378/115; 705/2
(58) Field of Classification Search
USPC .......................................................... 382/132
See application file for complete search history.

(56) References Cited

U.S. PATENT DOCUMENTS 6,501,827 B1 * 12/2002 Takasawa ...................... 378/116
7,142,632 B2 * 11/2006 Atzinger et al. ................ 378/62

FOREIGN PATENT DOCUMENTS

JP  2003-275194  9/2003

* cited by examiner

*Primary Examiner* — Hiep V Nguyen
(74) *Attorney, Agent, or Firm* — Fitzpatrick, Cella, Harper & Scinto (57) ABSTRACT

A radiographic imaging apparatus performs imaging based on an examination order including a plurality of imaging protocols, executes image processing for the captured image based on the imaging protocol used at the time of the imaging, designates a change source imaging protocol and a change destination imaging protocol from the examination order based on an instruction of an operator, and changes the imaging protocol corresponding to the image captured based on the change source imaging protocol from the change source imaging protocol to the change destination imaging protocol. When the change of protocol is made, the apparatus executes image processing based on the change destination imaging protocol for the image before the image processing which is captured based on the change source imaging protocol.

32 Claims, 8 Drawing Sheets

RADIOGRAPHIC IMAGING APPARATUS AND PROCESSING METHOD THEREFOR

BACKGROUND OF THE INVENTION

1. Field of the Invention

The present invention relates to a radiographic imaging apparatus and a processing method for the apparatus.

2. Description of the Related Art

Diagnoses and examinations based on imaging using radiation (for example, X-rays) have been actively practiced. Such an examination proceeds based on an examination order including a plurality of imaging protocols. In this case, an imaging protocol is manually created by, for example, a radiological technician in accordance with an examination order, and includes information such as the region of the patient's body to be imaged (the imaging region), imaging method, and image processing which are requested by the doctor.

An increasing number of hospitals have been adopting an online system using an HIS (Hospital Information System), RIS (Radiology Information System), and the like. In accordance with this trend, an externally created examination order is sometimes transferred to a radiographic imaging apparatus via a network. In this case, the operator selects an imaging protocol from the examination order displayed on the display unit of the radiographic imaging apparatus. The apparatus then sets parameters based on the imaging protocol and performs imaging based on the parameters.

Assume that the operator has selected the wrong imaging protocol, and the apparatus has executed imaging based on the selected protocol. In this case, since the set parameters are not appropriate, the apparatus cannot execute the intended imaging. As a means for solving this problem, the technique disclosed in Japanese Patent Laid-Open No. 2003-275194 is known.

The technique disclosed in Japanese Patent Laid-Open No. 2003-275194 allows to change the imaging protocol from one which has already been used for imaging to another imaging protocol. This technique, however, takes no consideration of a situation in which an examination proceeds based on an examination order, and hence does not allow changing to a pre-scheduled imaging protocol.

Even if, therefore, an examination order includes an imaging protocol as a change destination, it is not possible to change to that imaging protocol. For this reason, an examination order may redundantly include identical imaging protocols. When the operator is to re-execute imaging that has been erroneously executed (imaging based on an imaging protocol), he/she must perform the operation(s) required to add a new imaging protocol. This is cumbersome.

SUMMARY OF THE INVENTION

The present invention provides a technique which can easily cope with even a situation in which imaging based on an examination order has been executed by using a wrong imaging protocol.

According to a first aspect of the present invention there is provided a radiographic imaging apparatus which performs imaging based on an examination order including a plurality of imaging protocols, the apparatus comprising:

an imaging unit configured to perform the imaging by irradiating an object with radiation from a radiation generator and detecting radiation transmitted through the object using a radiation detector based on the imaging protocol;

an image processing unit configured to execute image processing for the captured image based on the imaging protocol used by the imaging unit to make the captured image;

a change source designation unit configured to designate a change source imaging protocol from the examination order based on an instruction from an operator;

a change destination designation unit configured to designate a change destination imaging protocol from the examination order based on an instruction from the operator; and a changing unit configured to change the imaging protocol corresponding to the image captured based on the change source imaging protocol from the change source imaging protocol to the change destination imaging protocol.

When the change is made by the changing unit, the image processing unit executes image processing based on the change destination imaging protocol for the image before the image processing which is captured based on the change source imaging protocol.

According to a second aspect of the present invention there is provided a processing method for a radiographic imaging apparatus which performs imaging based on an examination order including a plurality of imaging protocols, the method comprising:

causing an imaging unit to perform the imaging by irradiating an object with radiation from a radiation generator and detecting radiation transmitted through the object using a radiation detector based on the imaging protocol;

causing an image processing unit to execute image processing for the captured image based on the imaging protocol used by the imaging unit to make the captured image;

causing a change source designation unit to designate a change source imaging protocol from the examination order based on an instruction from an operator;

causing a change destination designation unit to designate a change destination imaging protocol from the examination order based on an instruction from the operator; and causing a changing unit to change the imaging protocol corresponding to the image captured based on the change source imaging protocol from the change source imaging protocol to the change destination imaging protocol.

When the change is made by the changing unit, the image processing unit executes image processing based on the change destination imaging protocol for the image before the image processing which is captured based on the change source imaging protocol.

Further features of the present invention will be apparent from the following description of exemplary embodiments with reference to the attached drawings.

DESCRIPTION OF THE EMBODIMENTS

An exemplary embodiment(s) of the present invention will now be described in detail with reference to the drawings. It should be noted that the relative arrangement of the components, the numerical expressions and numerical values set forth in these embodiments do not limit the scope of the present invention unless it is specifically stated otherwise. The following embodiments will exemplify a case in which X-rays are used as radiation. However, radiation is not limited to X-rays but may be other types of electromagnetic waves, or beams of α-particles, β-particles, or may be γ-rays.

First Embodiment

Figure 1:
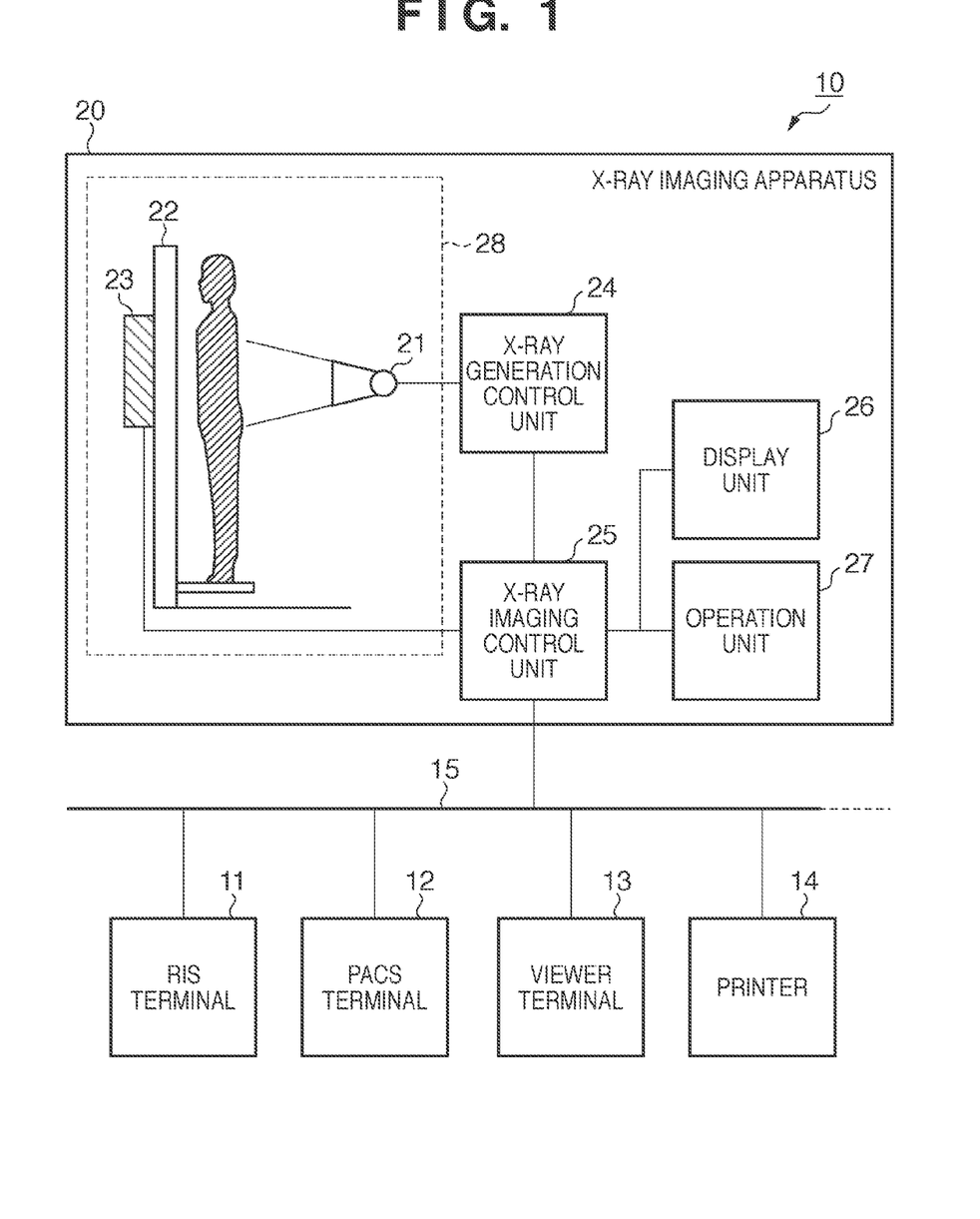
FIG. 1 is a block diagram showing an example of an X-ray imaging system 10 to which a radiographic imaging system according to an embodiment of the present invention is applied.

FIG. 1 is a block diagram showing an example of an X-ray imaging system 10 to which a radiographic imaging system according to an embodiment of the present invention is applied.

An X-ray imaging system 10 includes an RIS terminal 11, a PACS terminal 12, a viewer terminal 13, a printer 14, and an X-ray imaging apparatus 20. These apparatus are connected to each other via a communication 15 such as a network.

The RIS terminal 11 is an information system within a radiology department. The X-ray imaging apparatus 20 captures an X-ray digital image (to be referred to as a captured image hereinafter). The PACS terminal 12 stores and manages the images captured by the X-ray imaging apparatus 20. The viewer terminal 13 and the printer 14 output (display or print) a diagnosis image.

The X-ray imaging apparatus 20 executes an examination (imaging) based on an examination order constituted by a plurality of imaging protocols. In each imaging protocol, imaging conditions, the contents of image processing executed for a captured image, and the like are defined. More specifically, each imaging protocol includes various kinds of parameter information such as an imaging time and image processing time, sensor information, and imaging execution information.

The X-ray imaging apparatus 20 includes an imaging unit 28, an X-ray generation control unit 24, an X-ray imaging control unit 25, a display unit 26, and an operation unit 27.

The imaging unit 28 includes an X-ray tube 21, a sensor unit 22, and a sensor 23. In this case, the X-ray tube 21 functions as a radiation generator, and irradiates an object (that is, an object to be examined) with X-rays. The X-ray generation control unit 24 controls the generation of X-rays based on an imaging protocol. More specifically, the X-ray generation control unit 24 applies a voltage to the X-ray tube 21 to make it generate X-rays based on imaging conditions (for example, parameters such as a tube current, tube voltage, and irradiation period) corresponding to an imaging protocol.

The sensor 23 functions as a radiation detector, and detects X-rays transmitted through the object. The sensor unit 22 A/D-converts electric charge corresponding to the amount of X-rays transmitted through the object and detected by the sensor 23. The sensor unit 22 then transfers the result as a captured image to the X-ray imaging control unit 25. The X-ray imaging control unit 25 comprehensively controls X-ray imaging processing based on an imaging protocol. The X-ray imaging control unit 25 executes, for example, image processing (for example, correction processing, halftone processing, and frequency processing) for the captured image. The X-ray imaging control unit 25 performs image processing by using image processing parameters corresponding to the imaging protocol at the time of imaging operation.

The display unit 26 includes, for example, a display, and displays a system state and the like to the operator. The display unit 26 displays, for example, the examination order received from the RIS terminal 11 (the examination order created by the operator). The operation unit 27 includes, for example, a keyboard, mouse, and various kinds of buttons, and inputs instructions from the operator into the apparatus. The operation unit 27 inputs the designation of imaging protocols as a change source and a change destination into the apparatus.

Figure 2:
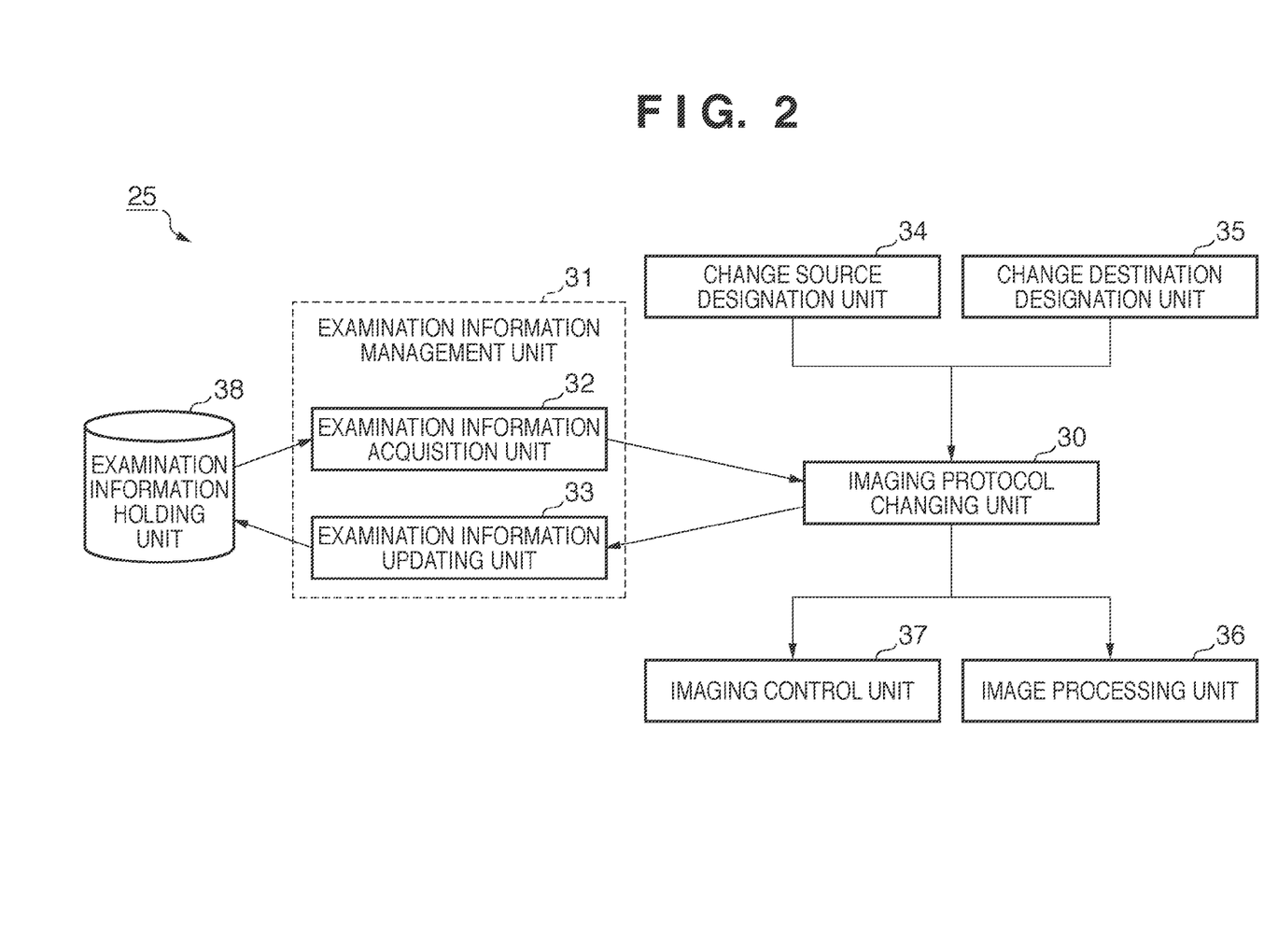
FIG. 2 is a block diagram showing an example of the functional arrangement of an X-ray imaging control unit 25 shown in FIG. 1.

An example of the functional arrangement of the X-ray imaging control unit 25 shown in FIG. 1 will be described with reference to FIG. 2.

The X-ray imaging control unit 25 includes an examination information management unit 31, an examination information holding unit 38, a change source designation unit 34, a change destination designation unit 35, an imaging protocol changing unit 30, an imaging control unit 37, and an image processing unit 36.

The image processing unit 36 executes image processing for a captured image. As described above, the image processing unit 36 performs this image processing by using image processing parameters corresponding to an imaging protocol.

The change source designation unit 34 designates an imaging protocol as a change target (change source) from the imaging protocols included in the examination order under execution. The change destination designation unit 35 designates an imaging protocol as a change target (change destination) from the imaging protocols included in the examination order under execution. Note that the change source designation unit 34 and the change destination designation unit 35 perform designation based on instructions from the operator via the operation unit 27.

The examination information management unit 31 manages various kinds of information associated with an examination under execution based on the examination order acquired from the RIS terminal 11 (or manually created by the operator). The examination information management unit 31 includes an examination information acquisition unit 32 and an examination information updating unit 33. The examination information acquisition unit 32 acquires the examination information under execution from the examination information holding unit 38. The examination information updating unit 33 updates the examination information held in the examination information holding unit 38.

The imaging protocol changing unit 30 changes the correspondence relationship between a captured image and an imaging protocol. More specifically, the imaging protocol changing unit 30 associates the image captured based on the imaging protocol designated as a change source by the change source designation unit 34 (before image processing) with the change destination imaging protocol designated by the change destination designation unit 35. With this operation, the apparatus processes the image by using image processing parameters corresponding to the change destination imaging protocol.

The imaging control unit 37 controls imaging based on the imaging protocol. When, for example, the imaging protocol changing unit 30 changes the imaging protocol, the imaging control unit 37 controls the execution of imaging based on the imaging protocol after the change.

Figure 3A:
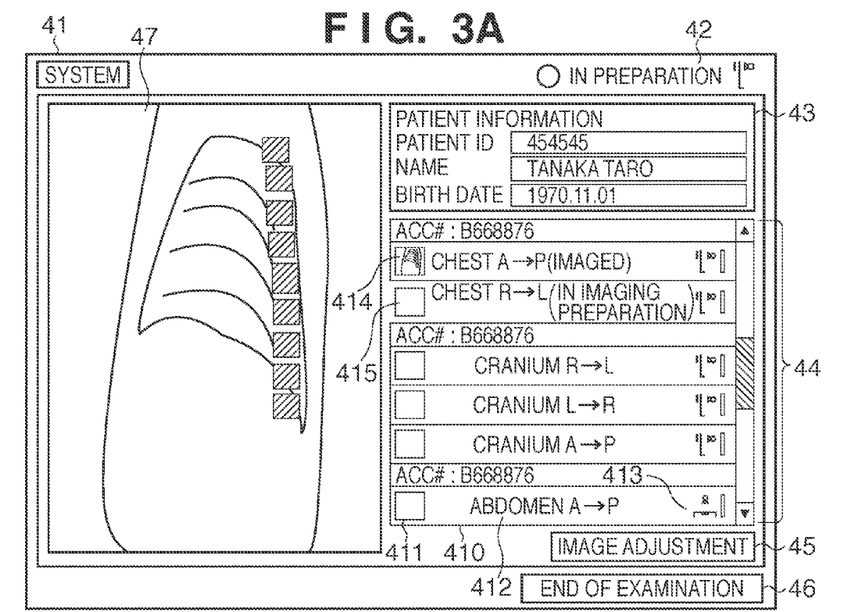
FIGS. 3A and 3B are views showing an example of an imaging protocol change window.
Figure 3B:
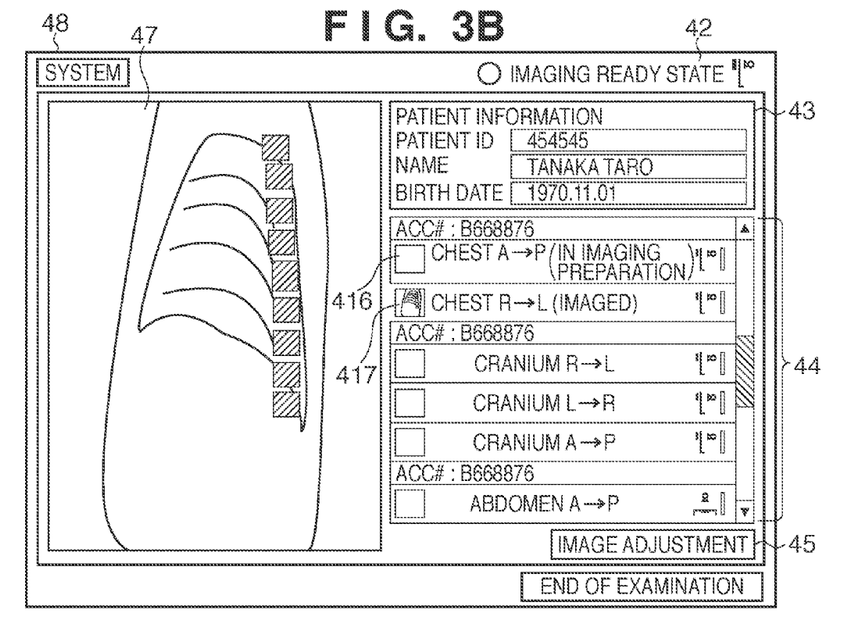

FIGS. 3A and 3B show an example of an imaging protocol change window. FIG. 3A shows a window 41 before the change of the imaging protocol. FIG. 3B shows a window 48 after the change of the imaging protocol. The windows shown in FIGS. 3A and 3B each include an object information display area 43 to display object information and a preview image display area 47 to display a captured image. Each window also includes an image adjustment button 45 to issue an instruction to adjust an image processing parameter for the captured image in preview and an examination end button 46 to issue an instruction to end an examination. Each window further includes an examination order display area 44 to indicate the information of an examination order under execution. An examination order display area 44 includes a plurality of imaging protocol buttons 410.

Each imaging protocol button 410 is provided with a thumbnail display area 411 to display the thumbnail of a captured image, a name display area 412 to display the name of an imaging region, and a sensor type display area 413 to display the information of a sensor type such as a standing-position type or decubitus type. The imaging protocol button 410 also indicates a state such as an imaged state (during preview), an imaging preparation state, and an imaging ready state. In addition, the windows shown in FIGS. 3A and 3B each include a sensor state display area 42 to indicate the state of a sensor associated with an imaging protocol under execution. Note that in the windows shown in FIGS. 3A and 3B, the states are indicated by characters. However, it is possible to indicate states by operating the GUI, for example, changing the colors of buttons and performing animation display.

A concrete example of a processing procedure according to the first embodiment will be described below. Assume that the operator has captured a chest R-L image while a chest A-P imaging protocol 414 is designated. In this case, the imaging direction is wrong, and hence image processing to be executed at the time of chest A-P imaging is performed for a captured chest R-L image.

The operator therefore designates the chest A-P imaging protocol 414 as a change source imaging protocol via the operation unit 27 to set a proper imaging protocol. The operator also designates a chest R-L imaging protocol 415 from the examination order display area 44 as a change destination via the operation unit 27.

Upon receiving this designation, the X-ray imaging apparatus 20 causes the imaging protocol changing unit 30 to associate the captured image with a chest R-L imaging protocol 417, as indicated by the window 48 after the change of the imaging protocol. With this operation, a thumbnail image of the captured image is displayed on the chest R-L imaging protocol 417. The X-ray imaging apparatus 20 also causes the image processing unit 36 to re-execute image processing by using the image processing parameters corresponding to the chest R-L imaging protocol 417. Thereafter, the X-ray imaging apparatus 20 updates the preview image in the preview image display area 47. An A-P imaging protocol 416 as a change source shifts to an imaging preparation state (that is, a non-imaged state), and the chest R-L imaging protocol 417 as a change destination shifts to an imaged state. In addition, the sensor state display area 42 shifts to an imaging ready state to allow imaging again.

The manner of designating imaging protocols as a change source and change destination is not specifically limited. For example, such an imaging protocol is designated by dragging and dropping a thumbnail image or an imaging protocol button or by dragging and dropping an image from the preview image display area 47 to a change destination imaging protocol button. If there are a plurality of examination orders for an examination under execution, the operator may be allowed to designate a change destination imaging protocol across examination orders.

Figure 4:
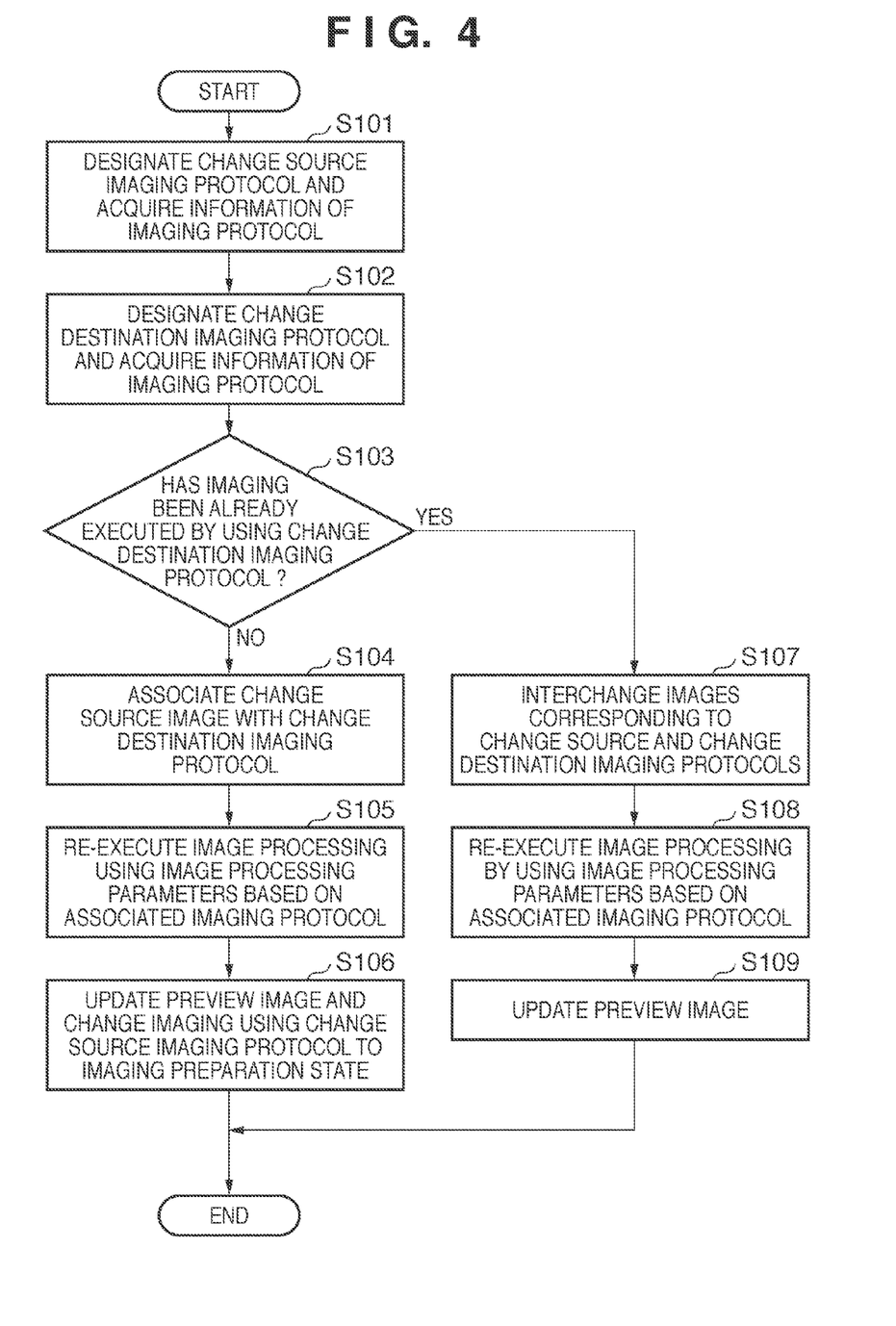
FIG. 4 is a flowchart showing an example of the operation of an X-ray imaging apparatus 20 shown in FIG. 1.

An example of the operation of the X-ray imaging apparatus 20 shown in FIG. 1 will be described next with reference to FIG. 4.

When starting imaging based on an examination order, an operator (for example, a radiology technician) presses the irradiation button. The X-ray imaging apparatus 20 then causes the X-ray tube 21 to irradiate an object with X-rays, and causes the sensor 23 to detect X-rays transmitted through the object. The X-ray imaging control unit 25 performs image processing such as correction processing, halftone processing, and frequency processing for the captured image obtained as a result of this operation.

When the display unit 26 displays the processed captured image afterward, the operator checks the image. Assume that as a result of this check, the operator has noticed an error in the imaging protocol. In this case, the operator inputs a change instruction via the operation unit 27 to correct the error. More specifically, the operator designates imaging protocols as a change source and a change destination. The X-ray imaging apparatus 20 then causes the change source designation unit 34 to designate an imaging protocol based on the instruction from the operator. That is, the change source designation unit 34 designates the imaging protocol as a change source which has been used for imaging. The X-ray imaging apparatus 20 causes the examination information acquisition unit 32 to acquire the information of the designated imaging protocol from the examination information holding unit 38 and notifies the imaging protocol changing unit 30 of the information (S101). Note that the information of the imaging protocol includes, for example, various kinds of parameter information such as an imaging time and an image processing time, sensor information, and imaging execution information.

Subsequently, the X-ray imaging apparatus 20 causes the change destination designation unit 35 to designate a change destination imaging protocol from the examination order under execution based on the instruction from the operator. The X-ray imaging apparatus 20 then causes the examination information acquisition unit 32 to acquire the information of the designated imaging protocol from the examination information holding unit 38, and notifies the imaging protocol changing unit 30 of the information (S102).

In this case, the X-ray imaging apparatus 20 causes the imaging protocol changing unit 30 to determine whether imaging has been executed by using the imaging protocol designated by the change destination designation unit 35. This determination is performed based on the information acquired in step S102. As a result of the determination, imaging using the imaging protocol has not been executed (NO in step S103), the X-ray imaging apparatus 20 causes the imaging protocol changing unit 30 to associate the image captured based on the change source imaging protocol with the imaging protocol designated as a change destination (S104). The X-ray imaging apparatus 20 causes the examination information updating unit 33 to update the information held in the examination information holding unit 38 (S104). The X-ray imaging apparatus 20 causes the image processing unit 36 to re-execute image processing for the image captured based on the change source imaging protocol (the image before image processing) by using image processing parameters corresponding to the change destination imaging protocol (S105). The X-ray imaging apparatus 20 then updates the preview image and displays it on the display unit 26. The X-ray imaging apparatus 20 also causes the imaging protocol changing unit 30 to shift the state of imaging based on the change source imaging protocol to the imagine preparation state (non-imaged state) and shift the imaging state based on the change destination imaging protocol to the imaged state. At this time, the X-ray imaging apparatus 20 shifts the preparation state of imaging by the sensor to the imaging ready state. The display unit 26 displays this state transition, as described with reference to FIGS. 3A and 3B (S106).

Upon determining in step S103 that the imaging based on the change destination imaging protocol has been executed (YES in step S103), the X-ray imaging apparatus 20 causes the imaging protocol changing unit 30 to interchange the images respectively associated with the change source and change destination imaging protocols. The examination information updating unit 33 then updates the information held in the examination information holding unit 38 (S107). The X-ray imaging apparatus 20 also causes the image processing unit 36 to re-execute image processing for each of the images captured based on the change source and change destination imaging protocols (each image before image processing) by using image processing parameters corresponding to the respective imaging protocols (S108). Thereafter, the X-ray imaging apparatus 20 updates the preview image and displays it on the display unit 26 (S109).

As described above, the first embodiment can easily cope with even a situation in which imaging based on an examination order has been executed by using a wrong imaging protocol. In addition, it is possible to easily perform imaging again by using an imaging protocol used for erroneous imaging. This makes it possible to prevent an excessive load from being applied to the operator even if imaging based on an examination order has been executed by using a wrong imaging protocol.

Second Embodiment

The second embodiment will be described next. The second embodiment will exemplify a case in which change conditions are provided at the time of changing an imaging protocol.

Figure 5:
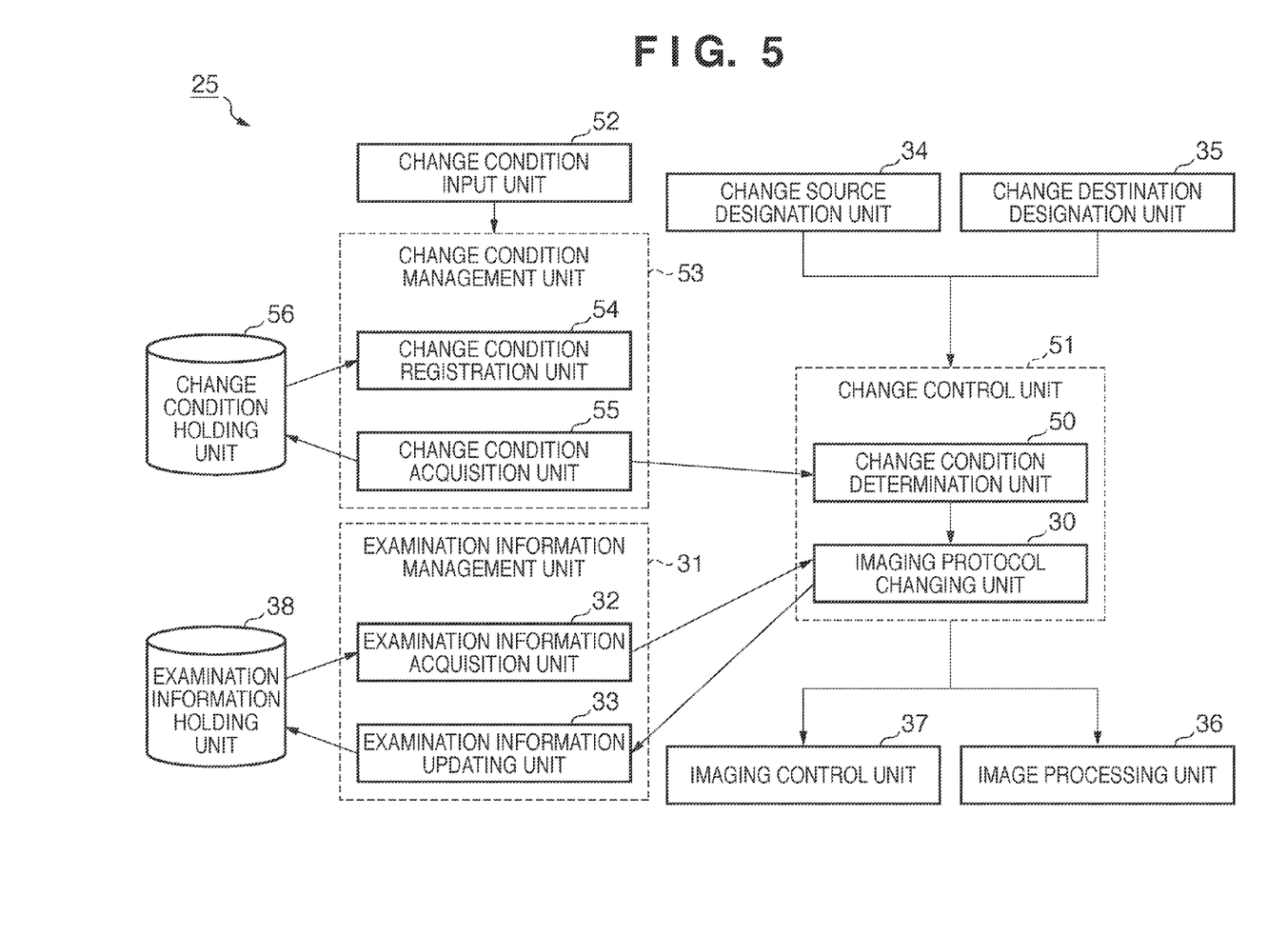
FIG. 5 is a block diagram showing an example of the functional arrangement of an X-ray imaging control unit 25 according to the second embodiment.

FIG. 5 is a view for explaining an example of the functional arrangement of an X-ray imaging control unit 25 according to the second embodiment. Note that the same reference numerals as in FIG. 2 explaining the first embodiment denote the same parts in FIG. 5.

A change condition input unit 52 inputs a change condition based on an instruction from the operator via an operation unit 27. A change condition holding unit 56 holds the change condition in correspondence with an imaging protocol. A change condition management unit 53 manages change conditions corresponding to each imaging protocol. The change condition management unit 53 includes a change condition registration unit 54 and a change condition acquisition unit 55. The change condition registration unit 54 registers the change condition input from the change condition input unit 52 in the change condition holding unit 56. The change condition acquisition unit 55 acquires a change condition held in the change condition holding unit 56. The change conditions held in the change condition holding unit 56 include information associated with the generation of X-rays (for example, a tube current, tube voltage, and irradiation period), sensor information indicating the type of sensor (for example, a standing-position/decubitus type), information associated with image processing, and information associated with a grid.

A change control unit 51 includes a change condition determination unit 50 which determines whether a change condition is satisfied and an imaging protocol changing unit 30 which performs changing processing based on the determination result.

Figure 6:
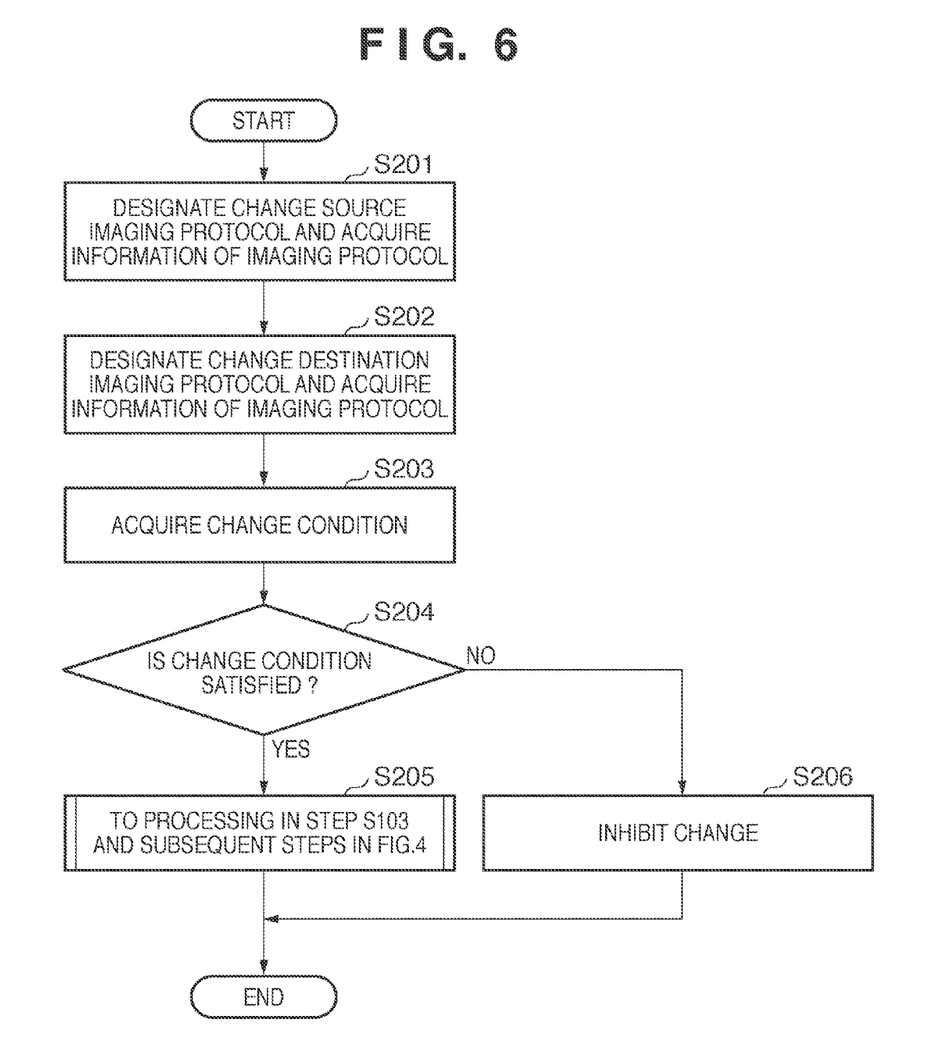
FIG. 6 is a flowchart showing an example of the operation of an X-ray imaging apparatus 20 according to the second embodiment.

FIG. 6 explains an example of the operation of an X-ray imaging apparatus 20 according to the second embodiment. For the sake of convenience, assume that imaging protocol change conditions are set in advance.

Assume that imaging based on an examination order has already started, and the operator has noticed an error in the imaging protocol as a result of a check on a captured image. In order to correct the error, the operator inputs a change instruction via the operation unit 27. More specifically, the operator designates imaging protocols as a change source and a change destination. The X-ray imaging apparatus 20 then causes a change source designation unit 34 to designate an imaging protocol based on the instruction from the operator. That is, the change source designation unit 34 designates the imaging protocol as a change source which has been used for imaging. The X-ray imaging apparatus 20 causes an examination information acquisition unit 32 to acquire the information of the designated imaging protocol from an examination information holding unit 38 (S201). As described above, the information of the imaging protocol includes, for example, various kinds of parameter information such as an imaging time and an image processing time, sensor information, and imaging execution information.

Subsequently, the X-ray imaging apparatus 20 causes a change destination designation unit 35 to designate a change destination imaging protocol from the examination order under execution based on the instruction from the operator. The X-ray imaging apparatus 20 causes the examination information acquisition unit 32 to acquire the information of the designated imaging protocol from the examination information holding unit 38 (S202).

The X-ray imaging apparatus 20 causes the change condition acquisition unit 55 to acquire the change conditions held in the change condition holding unit 56 (S203). The change condition determination unit 50 then checks whether the change destination imaging protocol acquired in step S202 satisfies the change conditions. If the change condition determination unit 50 determines as a result of the check that the change conditions are not satisfied (NO in step S204), the changing processing is inhibited. If the change conditions are satisfied (YES in step S204), the apparatus executes processing similar to that in the first embodiment. More specifically, the apparatus executes the processing in step S103 and the subsequent steps in FIG. 4.

A concrete example of a processing procedure according to the second embodiment will be described below. The radiology technician sets sensor type consistency and the like as change conditions in advance in the system setting window. Assume that the type of imaging based on an imaging protocol before change is a standing-position type, and the type of imaging based on a change destination imaging protocol is a supine type. In this case, since the change does not satisfy the condition, the processing is inhibited. It is possible to notify the technician of the inhibition of the change by, for example, displaying an inhibition icon or message on the imaging protocol button. Change conditions can include, for example, an X-ray irradiation period, tube voltage, tube current, and X-ray dose, and can also include sensor conditions. Note that it is possible to simultaneously set a plurality of such conditions.

As described above, the second embodiment allows to inhibit a change to an unintended imaging protocol as well as having the effects of the first embodiment. This can prevent the operator from erroneously making a change, and hence allows an examination to smoothly proceed.

Third Embodiment

The third embodiment will be described next. The third embodiment will exemplify a case in which after an imaging protocol is changed, the information of the change source imaging protocol is handed over to the change destination imaging protocol.

Figure 7:
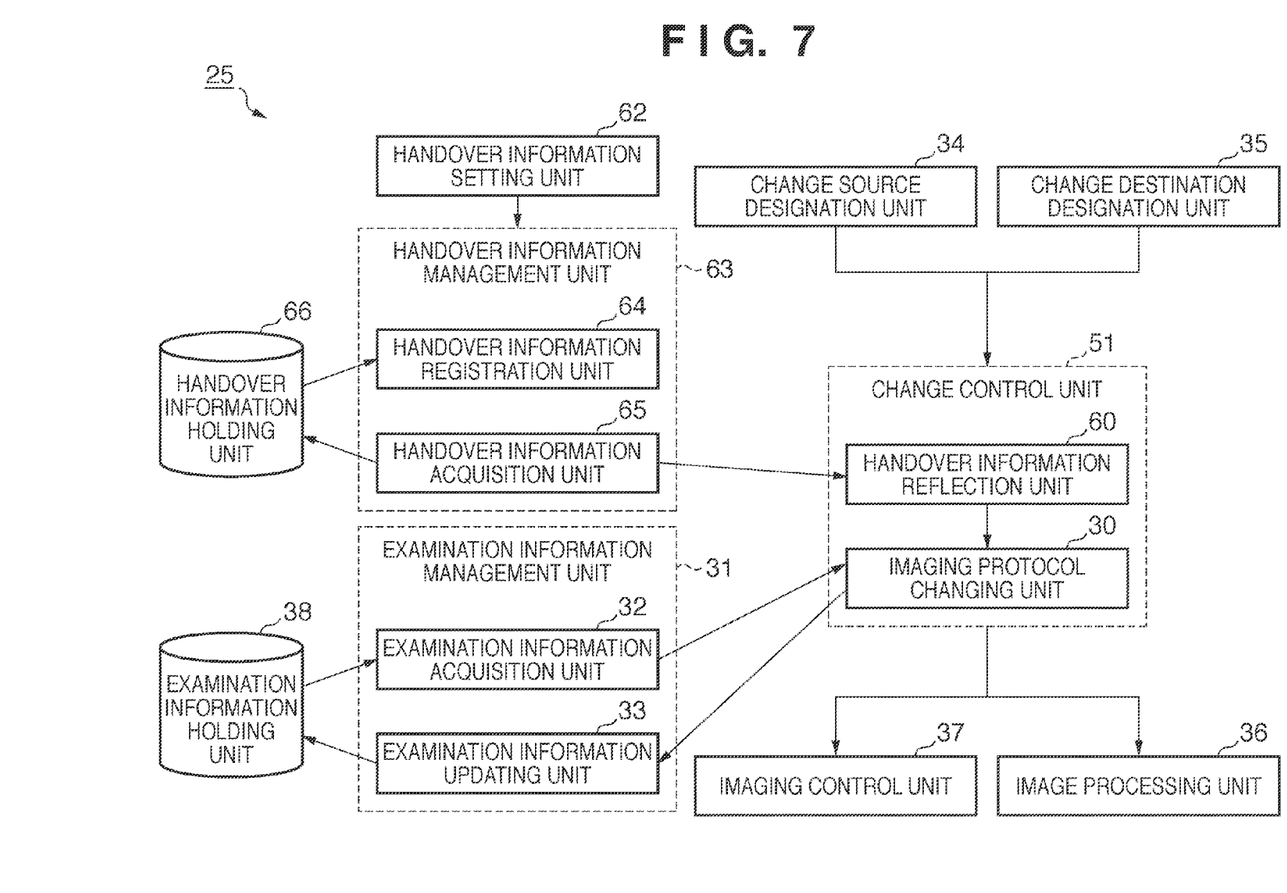
FIG. 7 is a block diagram showing an example of the functional arrangement of an X-ray imaging control unit 25 according to the third embodiment.

FIG. 7 explains an example of the functional arrangement of an X-ray imaging control unit 25 according to the third embodiment. Note that the same reference numerals as in FIGS. 2 and 5 explaining the first and second embodiments denote the same parts in FIG. 7.

A handover information setting unit 62 makes setting to determine which information in the information associated with an imaging protocol is to be handed over. This setting is made based on an instruction from the operator via an operation unit 27. Note that handover information includes information associated with the generation of X-rays (for example, a tube current, tube voltage, and irradiation period), sensor information indicating the type of sensor (for example, a standing-position/decubitus type), information associated with image processing, and information associated with a grid. For example, handover information includes information associated with image processing dependent on conditions at the time of imaging operation, for example, the presence/absence of a grid and the type of grid.

A handover information holding unit 66 holds handover information in correspondence with an imaging protocol. A handover information management unit 63 manages the handover information in correspondence with each of the imaging protocols. The handover information management unit 63 includes a handover information registration unit 64 and a handover information acquisition unit 65. The handover information registration unit 64 registers information corresponding to the handover information set by the handover information setting unit 62 in the handover information holding unit 66. The handover information acquisition unit 65 acquires the handover information held in the handover information holding unit 66. The change control unit 51 further includes a handover information reflection unit 60 which checks the presence/absence of handover information and executes reflection processing of the handover information based on the check result.

Figure 8:
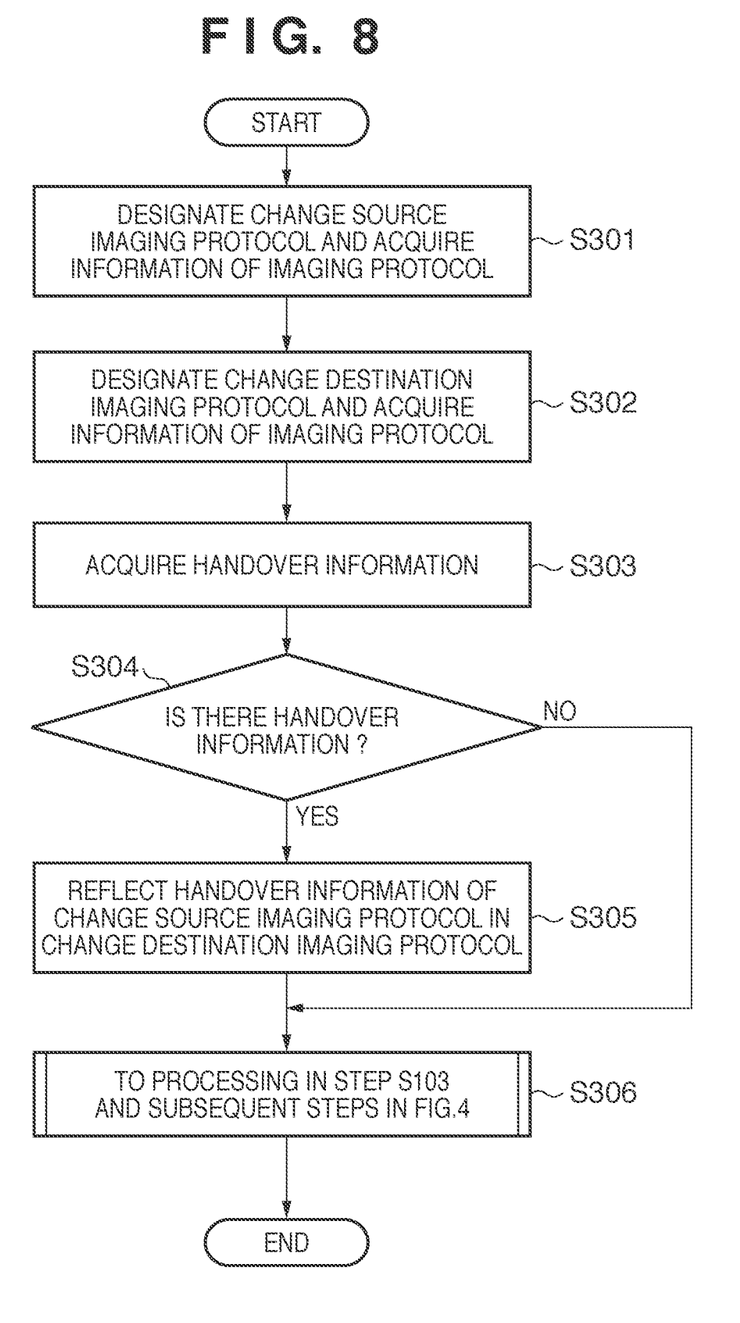
FIG. 8 is a flowchart showing an example of the operation of an X-ray imaging apparatus 20 according to the third embodiment.

FIG. 8 explains an example of the operation of an X-ray imaging apparatus 20 according to the third embodiment. For the sake of convenience, assume that handover information of an imaging protocol is set in advance.

Assume that imaging based on an examination order has already started, and the operator has noticed, as a result of checking the captured image, an error in the imaging protocol. In order to correct the error, the operator inputs a change instruction via the operation unit 27. More specifically, the operator designates imaging protocols as a change source and a change destination. The X-ray imaging apparatus 20 then causes a change source designation unit 34 to designate an imaging protocol based on the instruction from the operator. That is, the change source designation unit 34 designates the imaging protocol as a change source which has been used for imaging. The X-ray imaging apparatus 20 causes an examination information acquisition unit 32 to acquire the information of the designated imaging protocol from an examination information holding unit 38 (S301). As described above, the information of the imaging protocol includes, for example, various kinds of parameter information such as an imaging time and an image processing time, sensor information, and imaging execution information.

The X-ray imaging apparatus 20 then causes a change destination designation unit 35 to designate a change destination imaging protocol from the examination order under execution based on an instruction from the operator. The examination information acquisition unit 32 acquires the information of the designated imaging protocol from the examination information holding unit 38 (S302).

The X-ray imaging apparatus 20 causes the handover information acquisition unit 65 to acquire handover information associated with the change source imaging protocol from the handover information holding unit 66 (S303). The handover information reflection unit 60 then checks whether any handover information is acquired in step S302. If there is no handover information (NO in step S304), the X-ray imaging apparatus 20 executes processing similar to that in the first embodiment. More specifically, the X-ray imaging apparatus 20 executes the processing in step S103 and the subsequent steps in FIG. 4. If any handover information is acquired (YES in step S304), the handover information is reflected in the change destination imaging protocol, and then processing similar to that in the first embodiment is executed.

A concrete example of a processing procedure according to the third embodiment will be described below. A radiological technician sets handover information and the like in a system setting window or the like in advance. Assume that this handover information is grid information. Assume that in this state, the radiological technician has erroneously captured a chest R-L image while a chest A-P imaging protocol 414 is designated. In this case, the imaging protocol is inconsistent with the imaging direction. For this reason, image processing which should be executed at the time of capturing a chest A-P image has been executed for a captured chest R-L image. The operator therefore designates a chest A-P imaging protocol 414 as a change source imaging protocol via the operation unit 27 to set a proper imaging protocol. The operator designates the chest R-L imaging protocol 415 from the examination order display area 44 as a change destination via the operation unit 27. At this time, the handover information reflection unit 60 reflects, in the chest R-L imaging protocol 415 as a change destination, the setting indicating the presence of a grid in the chest A-P imaging protocol 414 as a change source.

As described above, according to the third embodiment, the information of a change source imaging protocol is handed over to a change destination imaging protocol. This can save the trouble of adjusting image processing after the change of an imaging protocol, and hence can reduce the load on the operator accompanying the change of an imaging protocol.

The typical embodiments of the present invention have been described above. However, the present invention is not limited to the embodiments described above and shown in the accompanying drawings, and can be modified and executed as needed within the spirit and scope of the invention. For example, the arrangements described in the second and third embodiments may be combined and executed.

In addition, the present invention can take embodiments as a system, apparatus, method, program, storage medium, and the like. More specifically, the present invention can be applied to a system including a plurality of devices, or to an apparatus including a single device.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (for example, computer-readable storage medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-201094 filed on Aug. 31, 2009, which is hereby incorporated by reference herein in its entirety.

What is claimed is:

1. A radiographic imaging apparatus which performs imaging based on an examination order including a plurality of imaging protocols, the apparatus comprising:
   an imaging unit configured to perform the imaging by irradiating an object with radiation from a radiation generator and detecting radiation transmitted through the object using a radiation detector based on a first imaging protocol;
   an image processing unit configured to execute image processing for a captured image based on the first imaging protocol, which is used at the time of imaging by said imaging unit;
   a change source designation unit configured to designate a change source imaging protocol from the examination order based on an instruction from an operator, the change source imaging protocol being the first imaging protocol;
   a change destination designation unit configured to designate a change destination imaging protocol from the examination order based on an instruction from the operator; and
   a changing unit configured to change the imaging protocol corresponding to the image captured based on the change source imaging protocol from the change source imaging protocol to the change destination imaging protocol,
   wherein, in a case where the change is made by said changing unit, said image processing unit executes image processing based on the change destination imaging protocol for the image which is captured based on the change source imaging protocol.

2. The apparatus according to claim 1, wherein, in a case where making the change if imaging based on the change destination imaging protocol has not been executed, said changing unit shifts an imaging state based on the change source imaging protocol to a non-imaged state, and shifts an imaging state based on the change destination imaging protocol to an imaged state.

3. The apparatus according to claim 2, wherein, in a case of shifting an imaging state based on the change destination imaging protocol to an imaged state, said changing unit shifts an imaging state by said imaging unit from an imaging preparation state to an imaging ready state.

4. The apparatus according to claim 1, wherein said changing unit changes the imaging protocol corresponding to the image captured based on the change destination imaging protocol from the change destination imaging protocol to the change source imaging protocol in a case where imaging based on the change destination imaging protocol has been executed, and
   said image processing unit executes image processing based on the change source imaging protocol for the image which is captured based on the change destination imaging protocol, in a case where the change is made if imaging based on the change destination imaging protocol has been executed.

5. The apparatus according to claim 1, further comprising a change condition management unit configured to manage a change condition at the time of the change by said changing unit in correspondence with the imaging protocol, and
   a determination unit configured to determine whether the change destination imaging protocol at the time of the change by said changing unit satisfies the change condition managed by said change condition management unit,
   wherein said changing unit makes the change in a case where said determination unit determines that the change destination imaging protocol satisfies the change condition.

6. The apparatus according to claim 5, wherein said change condition includes a condition corresponding to at least one of information of the radiation generator, information of the radiation detector, information of image processing by said image processing unit, and information associated with a grid.

7. The apparatus according to claim 1, further comprising:
   a handover information management unit configured to manage handover information to be handed over from the change source imaging protocol to the change destination imaging protocol at the time of the change made by said changing unit in correspondence with the imaging protocol; and
   a reflection unit configured to reflect the handover information managed by said handover information management unit at the time of the change made by said changing unit in the change destination imaging protocol.

8. The apparatus according to claim 7, wherein the handover information includes at least one of information of the radiation generator, information of the radiation detector, information of image processing by said image processing unit, and information associated with a grid.

9. The apparatus according to claim 1, wherein the imaging protocol includes at least one of information of the radiation generator, information of the radiation detector, information of image processing by said image processing unit, and information associated with a grid.

10. A processing method for a radiographic imaging apparatus which performs imaging based on an examination order including a plurality of imaging protocols, the method comprising:
   performing the imaging by irradiating an object with radiation from a radiation generator and detecting radiation transmitted through the object using a radiation detector based on a first imaging protocol;
   executing image processing for a captured image based on the first imaging protocol, which is used at the time of performing the imaging;
   designating a change source imaging protocol from the examination order based on an instruction from an operator, the change source imaging protocol being the first imaging protocol;
   designating a change destination imaging protocol from the examination order based on an instruction from the operator; and changing the imaging protocol corresponding to the image captured based on the change source imaging protocol from the change source imaging protocol to the change destination imaging protocol, wherein, in a case where the change is made in said changing step, image processing based on the change destination imaging protocol is performed for the image which is captured based on the change source imaging protocol.

11. An imaging control apparatus comprising:
a display control unit configured to display, on a display unit, a plurality of pieces of imaging protocol information;
a designation unit configured to designate a first imaging protocol and a second imaging protocol; and
a control unit configured to associate, in a case where imaging using one imaging protocol of the first imaging protocol and the second imaging protocol has not been executed, an image captured based on the other imaging protocol with the one imaging protocol, and to interchange, in a case where imaging using the first imaging protocol and the second imaging protocol has been executed, respective images associated with the first imaging protocol and the second imaging protocol,
wherein said display control unit displays, on the display unit, the first and second imaging protocols and the image associated with the one imaging protocol.

12. The apparatus according to claim 11, wherein said designation unit designates an imaging protocol of a change destination and an imaging protocol of a change source with which a captured image is associated, and
in a case where imaging using the imaging protocol of the change destination has not been executed, said control unit associates a captured image associated with the imaging protocol of the change source with the imaging protocol of the change destination.

13. The apparatus according to claim 11, wherein said designation unit designates an imaging protocol of a change destination and an imaging protocol of a change source with which a captured image is associated, and
in a case where imaging using the imaging protocol of the change destination has been executed, said control unit interchanges respective images associated with the first imaging protocol and the second imaging protocol.

14. The apparatus according to claim 11, wherein said control unit associates an image captured based on the other imaging protocol with the one imaging protocol, and shifts an imaging state based on the other imaging protocol to a non-imaged state.

15. The apparatus according to claim 14, wherein said display control unit changes a display of at least one of the first and second imaging protocols in accordance with the shift of the imaging state.

16. The apparatus according to claim 11, wherein said control unit associates an image captured based on the other imaging protocol with the one imaging protocol, and shifts an imaging state based on the one imaging protocol to an imaged state.

17. The apparatus according to claim 16, wherein said display control unit changes a display of at least one of the first and second imaging protocols in accordance with the shift of the imaging state.

18. The apparatus according to claim 11, further comprising a processing unit configured to perform image processing for respective images associated with the first imaging protocol and the second imaging protocol, based on image processing conditions corresponding respectively to the first imaging protocol and the second imaging protocol.

19. The apparatus according to claim 18, wherein said processing unit performs the image processing in accordance with a change of an association between the first imaging protocol and the second imaging protocol.

20. The apparatus according to claim 18, further comprising a holding unit configured to an image on which the image processing is performed by said processing unit,
wherein said processing unit performs the image processing corresponding to a changed imaging protocol.

21. The apparatus according to claim 11, wherein the image is a reduced image generated from the captured image.

22. The apparatus according to claim 11, wherein the imaging protocol includes information of an imaging condition for capturing an image.

23. The apparatus according to claim 11, wherein the first imaging protocol and the second imaging protocol include information of an image processing condition of the captured image.

24. The apparatus according to claim 11, further comprising an acquisition unit configured to acquire, as the captured image, digital radiation image data based on the first imaging protocol and the second imaging protocol from a digital radiation imaging unit having a plurality of pixels which convert radiation to electric signal.

25. The apparatus according to claim 11, wherein said designation unit designates the first imaging protocol and the second imaging protocol in accordance with an operation input to an operation unit.

26. The apparatus according to claim 11, wherein said display control unit displays the first imaging protocol and the second imaging protocol and reduced images of the images associated with the first imaging protocol and the second imaging protocol.

27. The apparatus according to claim 26, wherein a display window displayed by said display control unit has a first display area to display the first imaging protocol and the second imaging protocol and the reduced images, and a second display area to display an image having a size larger than each size of the reduced images.

28. The apparatus according to claim 27, wherein after image processing corresponding to the one imaging protocol has been executed, said display control unit displays an image on which the image processing has been executed on the second display area.

29. A processing method for an imaging control apparatus that includes at least a processor and a memory, the method comprising:
displaying, on a display unit, a plurality of pieces of imaging protocol information;
designating a first imaging protocol and a second imaging protocol by means of the processor;
associating by means of the processor, in a case where imaging using one imaging protocol of the first imaging protocol and the second imaging protocol has not been executed, an image captured based on the other imaging protocol with the one imaging protocol, and interchanging by means of the processor, in a case where imaging using the first imaging protocol and the second imaging protocol has been executed, respective images associated with the first imaging protocol and the second imaging protocol,
wherein said displaying step includes displaying, on the display unit, the first and second imaging protocols and the image associated with the one imaging protocol.

30. An imaging control system comprising:
a display control unit configured to display, on a display unit, a plurality of pieces of imaging protocol information;
a designation unit configured to designate a first imaging protocol and a second imaging protocol;
a control unit configured to associate, in a case where imaging using one imaging protocol of the first imaging protocol and the second imaging protocol has not been executed, an image captured based on the other imaging protocol with the one imaging protocol, and to interchange, in a case where imaging using the first imaging protocol and the second imaging protocol has been executed, respective images associated with the first imaging protocol and the second imaging protocol; and
an acquisition unit configured to acquire, as a captured image, digital radiation image data based on the first imaging protocol and the second imaging protocol from a digital radiation imaging unit having a plurality of pixels which convert radiation to electric signal.

31. A non-transitory computer-readable storage medium storing a program for causing a computer to execute a processing method comprising:
performing the imaging by irradiating an object with radiation from a radiation generator and detecting radiation transmitted through the object using a radiation detector based on a first imaging protocol;
executing image processing for a captured image based on the first imaging protocol, which is used at the time of performing the imaging;
designating a change source imaging protocol from the examination order based on an instruction from an operator, the change source imaging protocol being the first imaging protocol;
designating a change destination imaging protocol from the examination order based on an instruction from the operator; and
changing the imaging protocol corresponding to the image captured based on the change source imaging protocol from the change source imaging protocol to the change destination imaging protocol,
wherein, in a case where the change is made in the changing step, image processing based on the change destination imaging protocol is performed for the image which is captured based on the change source imaging protocol.

32. A non-transitory computer-readable storage medium storing a program for causing a computer to execute a processing method comprising:
displaying, on a display unit, a plurality of pieces of imaging protocol information;
designating a first imaging protocol and a second imaging protocol;
associating, in a case where imaging using one imaging protocol of the first imaging protocol and the second imaging protocol has not been executed, an image captured based on the other imaging protocol with the one imaging protocol, and interchanging, in a case where imaging using the first imaging protocol and the second imaging protocol has been executed, respective images associated with the first imaging protocol and the second imaging protocol,
wherein the displaying step includes displaying, on the display unit, the first and second imaging protocols and the image associated with the one imaging protocol.

* * * * *